(12) United States Patent
Casutt

(10) Patent No.: US 9,107,702 B2
(45) Date of Patent: Aug. 18, 2015

(54) CENTRAL STRUCTURES SPREADER FOR THE LUMBAR SPINE

(75) Inventor: Guido Casutt, Rickenbach-Sulz (CH)

(73) Assignee: Zimmer GmbH, Winterthur (CH)

( * ) Notice: Subject to any disclaimer, the term of this patent is extended or adjusted under 35 U.S.C. 154(b) by 2690 days.

(21) Appl. No.: 11/671,615

(22) Filed: Feb. 6, 2007

(65) Prior Publication Data

US 2008/0188856 A1 Aug. 7, 2008

(51) Int. Cl.
*A61B 17/66* (2006.01)
*A61B 17/80* (2006.01)
*A61B 17/70* (2006.01)

(52) U.S. Cl.
CPC .............. *A61B 17/70* (2013.01); *A61B 17/7031* (2013.01); *A61B 17/7059* (2013.01); *A61B 17/8009* (2013.01)

(58) Field of Classification Search
CPC ........... A61B 17/8004; A61B 17/8009; A61B 17/8023; A61B 17/7031; A61B 17/7059
USPC ...................... 606/70–71, 247–249, 280–299; 623/17.11–17.16
See application file for complete search history.

(56) References Cited

U.S. PATENT DOCUMENTS

| | | | |
|---|---|---|---|
| 6,093,201 A * | 7/2000 | Cooper et al. | 606/232 |
| 6,852,113 B2 * | 2/2005 | Nathanson et al. | 606/71 |
| 6,989,011 B2 | 1/2006 | Paul et al. | |
| 7,029,475 B2 | 4/2006 | Panjabi | |
| 7,087,056 B2 | 8/2006 | Vaughan | |
| 7,101,375 B2 | 9/2006 | Zucherman et al. | |
| 2001/0047174 A1 | 11/2001 | Donno et al. | |
| 2006/0135959 A1 | 6/2006 | Yuan et al. | |
| 2007/0239158 A1 | 10/2007 | Trieu et al. | |

FOREIGN PATENT DOCUMENTS

| | | |
|---|---|---|
| EP | 0669109 B1 | 8/1995 |
| EP | 1 836 972 A | 9/2007 |
| NL | 7610576 | 12/2007 |
| WO | 2005037110 A | 4/2005 |
| WO | 2006042206 A2 | 4/2006 |
| WO | 2006049993 A | 5/2006 |

\* cited by examiner

*Primary Examiner* — Matthew Lawson
(74) *Attorney, Agent, or Firm* — Seager, Tufte & Wickhem LLC

(57) ABSTRACT

A spinal device and associated method are provided for spreading of first and second vertebral elements, each of the first and second vertebral elements having a circumferential surface defining a vertebral body and a pedicle having a pedicle root portion adjacent the circumferential surface. The device includes a first end member having at least one surface adapted to conform to at least one of the circumferential surface and the pedicle root portion of the first vertebral element, and a second end member having at least one surface adapted to conform to at least one of the circumferential surface and the pedicle root portion of the second vertebral element. The device further includes a resilient member extending between the first and second end members and being adapted to exert a force against the first and second vertebral elements.

11 Claims, 3 Drawing Sheets

CENTRAL STRUCTURES SPREADER FOR THE LUMBAR SPINE

FIELD OF THE INVENTION

The invention relates generally to spinal surgery and, more particularly, to systems and methods for restoring the volume of one or more of intervertebral foramen within a lumbar spine segment.

BACKGROUND OF THE INVENTION

An intervertebral foramen is an aperture extending generally laterally from the spinal canal dimensioned to accommodate the exiting nerve roots from the spinal cord at a given vertebral level in the spine. Within a single vertebral level, an intervertebral foramen is defined anteriorly by the annulus of the intervertebral disc and the posterior and lateral aspects of the adjacent superior and inferior vertebral bodies, superiorly by the pedicle of the superior vertebra, inferiorly by the pedicle of the inferior vertebra, and posteriorly by the facet joint formed by the inferior articulating facet of the superior vertebra and the superior articulating facet of the inferior vertebra. In a normal, non-pathologic spine, the intervertebral foramen is dimensioned such that the exiting nerve roots are adequately protected from compression and/or other undesirable contact during flexion, extension, lateral bending, and axial rotation of the particular vertebral level. This protection is provided by maintaining the volume of the intervertebral foramen during (or promptly restored after) such movements, as well as under the axial loading that occurs at that vertebral level during activities of daily living.

The spatial integrity or volume of the intervertebral foramen may become compromised due to any of a number of events or pathologies, resulting in a constriction or narrowing of one or more aspects of the intervertebral foramen. These may include, but are not necessarily limited to, degenerative disc disease, disc failure or rupture due to trauma, osteophyte formation and/or calcification of the ligamentum flavum, intervertebral osteochondrosis, scoliosis, and/or destabilization from spine surgery procedures (e.g. discectomy, fusion, total disc replacement, nucleus replacement). When this occurs, the resulting narrowing or constriction ("lateral stenosis") may cause the exiting nerve root to be compressed by one or more of the aspects that define the intervertebral foramen. Depending on the severity of the condition, this may cause any of a host of problems for the patient, including shooting pain (radiculopathy) and/or impaired motor or sensory nerve function due to the nerve compression. Moreover, the superior and inferior articulating facets may become misaligned ("facet imbrication") and/or be undesirably compressed against one another, either condition which may be painful and/or adversely affect the proper function of the facet joint.

A variety of techniques have been developed over time for treating spinal pathologies, some of which have the effect of restoring the volume of the intervertebral foramen, but which may be limited by the path of nerve roots extending from the spine. Known techniques for example, do so indirectly through the use of procedures or implants in aspects of the spine remote to or outside of the intervertebral foramen. These procedures include, but are not necessarily limited to, the use of pedicle screw systems (fixed or dynamic) extending between adjacent pedicles, spinous process spacer systems positioned between adjacent spinous processes, plating systems (lateral and/or anterior) coupled between adjacent vertebral bodies, and intervertebral implants (e.g. fusion, total disc replacement, nucleus replacement) positioned between adjacent vertebral bodies. None of these systems or procedures restores the intervertebral foramen volume in a direct manner. Moreover, many of these procedures involve fusing or rigidly affixing the adjacent levels of the spine, such as via interbody fusion, posterior fusion, fusion via plating and/or fusion of the facet joint itself, each of which may limit normal physiologic motion.

A system capable of directly restoring the volume of an intervertebral foramen while not interfering with the path of nerve roots and other anatomical structures is therefore desirable.

SUMMARY OF THE INVENTION

In accordance with an embodiment of the invention, a spinal device is provided for spreading of first and second vertebral elements, each of the first and second vertebral elements having a circumferential surface defining a vertebral body and a pedicle having a pedicle root portion adjacent the circumferential surface. The device includes a first end member having at least one surface adapted to conform to at least one of the circumferential surface and the pedicle root portion of the first vertebral element, and a second end member having at least one surface adapted to conform to at least one of the circumferential surface and the pedicle root portion of the second vertebral element. The device further includes a resilient member extending between the first and second end members and being adapted to exert a force against the first and second vertebral elements.

In other embodiments, the device may include a resilient member having polycarbonate urethane or include first and second end members each having at least one aperture. The aperture in such embodiments may be adapted to direct a bone anchor into at least one of the pedicle root portion and the vertebral body. The first end member may further have a main body portion and the at least one aperture may be laterally offset from the main body portion. In another aspect of the present invention, the spinal device may include a first end member having an exposed surface angled to be in a confronting relationship with an intervertebral foramen such that the at least one aperture extends from the exposed surface.

In another embodiment, a method of spreading first and second vertebral elements apart is provided, with each of the first and second vertebral elements having a circumferential surface defining a vertebral body and a pedicle having a pedicle root portion adjacent the circumferential surface. The method may include the steps of providing a spreading device having first and second end members and a resilient member there between, conforming at least one surface of the first end member against at least one of the circumferential surface and the pedicle root portion of the first vertebral element, and conforming at least one surface of the second end member against at least one of the circumferential surface and the pedicle root portion of the second vertebral element. The method may also include the step of directing a first bone anchor through the at least one aperture in the first end member and into at least one of the pedicle root portion and the vertebral body of the first vertebral element, and directing a second bone anchor through the at least one aperture in the second end member and into at least one of the pedicle root portion and the vertebral body of the second vertebral element.

A method may also include the steps of threadably engaging the first bone anchor with the at least one of the pedicle root portion and the vertebral body of the first vertebral body, ratchetly engaging the resilient member with at least one of the first and second end members, and ratchetly adjusting the position of the resilient member with respect to at least one of the first and second end members.

Advantageously, the embodiments provide a device and corresponding method capable of directly restoring the volume of an intervertebral foramen while not interfering with the path of nerve roots and other anatomical structures. Moreover, by conforming end members to vertebral surfaces defining or lying adjacent the intervertebral foramen, these embodiments permit improved coupling of the device to such surfaces. The devices according to various embodiments of this invention allow for the implant location to be more laterally located relative to the foramen. As a result, this invention allows for distraction outside (lateral) of the foramen which permits the use of larger, more robust devices that may be of less rigid materials than existing devices.

Prior art devices that are placed in the foraminal space risk impacting or contacting the nerve root. Additionally, prior art rigid devices, when used bilaterally, limit the segmental range of motion. The present invention allows for increased segmental motion and the use of appropriate materials (PCU and the like).

Moreover, prior art devices often utilize a flange and an aperture for mounting; whereas, the present invention utilizes bone screws into the cortical area for a more stable connection while allowing for rotational movement between segments. The present invention also offers the advantage of covering the disc opening caused by a prolapse and may prevent a bulged disc.

BRIEF DESCRIPTION OF THE DRAWINGS

These and other objectives and advantages will become readily apparent to those of ordinary skill in the art from the following description of embodiments of the invention and from the drawings in which.

DETAILED DESCRIPTION

Figure 1:
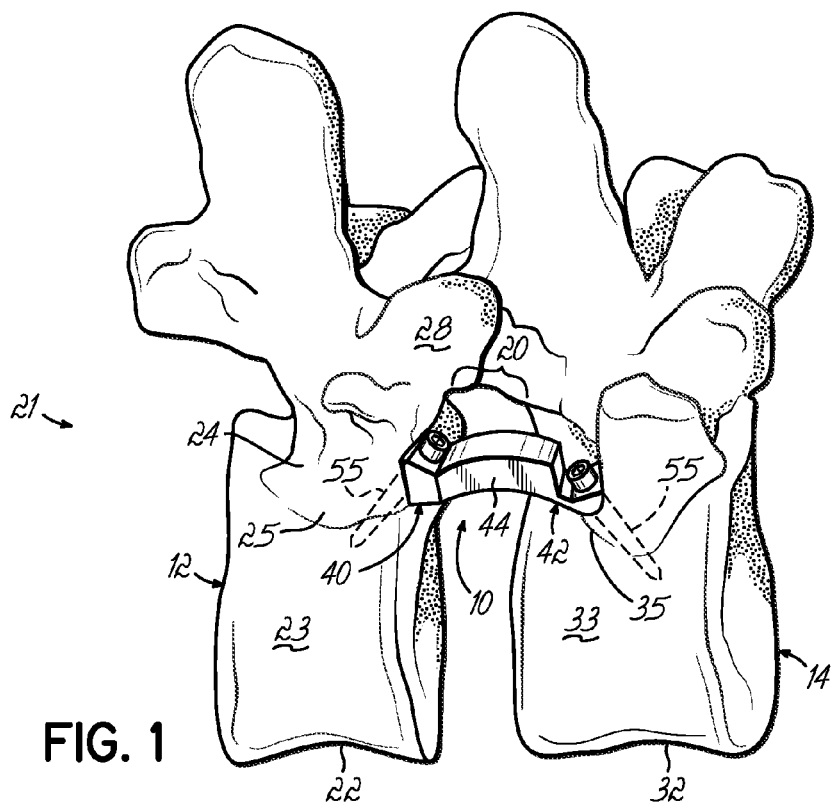
FIG. 1 is a perspective view of a spreading device implanted in an intervertebral foramen.

With reference to the figures and, more particularly to FIG. 1, a spreading device 10 is shown implanted within an intervertebral foramen 20 of a human spine 21. For purposes of simplicity, the spreading device 10 will be described in the context of a single vertebral level with unilateral implantation. Persons of ordinary skill in the art, however, will appreciate the fact that the spreading device 10 may be used in multiple vertebral levels and further with bi-lateral implantation. The single vertebral level depicted for illustrative purposes includes an inferior vertebra 12, a superior vertebra 14 and an intervertebral disc (not shown for simplicity of illustration). The inferior vertebra 12 includes a vertebral body 22 having a first outer circumferential surface 23, a pedicle 24 having a pedicle root portion 25, and an inferior facet 28. The superior vertebra 14 includes a vertebral body 32 having a second outer circumferential surface 33, a pedicle 34 having a pedicle root portion 35 and a superior facet 36 (see FIG. 3). The intervertebral foramen 20 is defined by the posterior aspect or annulus of the disc (not shown), portions of posterior aspect of the inferior vertebral body 22, portions the inferior aspect of the inferior pedicle 24, portions of the anterior aspect of the inferior facet 28 of the inferior vertebra 12, portions of the anterior aspect of the superior facet 36 of the superior vertebra 14 and portions of the superior aspect of the superior pedicle 34.

Figure 1A:
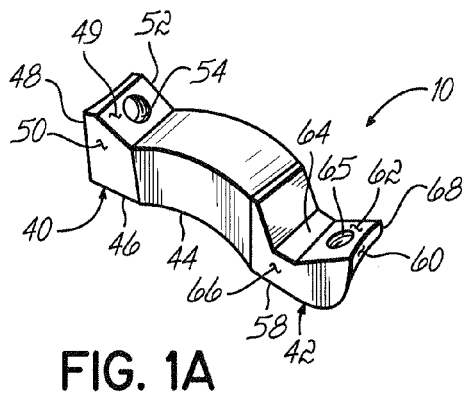
FIG. 1A is a perspective view of the spreading device of FIG. 1.

With reference to FIGS. 1-1A, the spreading device 10 is a generally elongate body defined by two opposed first and second end members 40, 42 and a resilient central portion 44 there between. The spreading device 10 is shown deployed in a generally linear cephalo-caudal relationship between the inferior and superior vertebrae 12, 14 such that the first and second end members 40, 42 are respectively in a confronting relationship with the first and second outer circumferential surfaces 23, 33 of the inferior and superior vertebrae 12, 14. Each of the first and second end members 40, 42 is irregularly shaped. The first end member 40 includes a posterior surface 46, distal surface 48, angled surface 49 and lateral surfaces 50, 52. The posterior surface 46 is shaped to conform over the first outer circumferential surface 23 of the vertebral body 22 of the inferior vertebra 12. The distal surface 48, which is adjacent the posterior surface 46, is shaped to conform to the surface on the pedicle root portion 25 of the inferior pedicle 24. An angled surface 49 lies opposed from the posterior face 46. The angled surface 49 is suitably shaped and dimensioned to allow insertion of an anchor such as a screw 55 (shown in phantom) generally from the intervertebral foramen region, into and through the body of the first end member 40, and the pedicle 24. The angled surface 49 further includes an aperture 54 adapted to threadably receive the screw 55. Alternatively, the aperture 55 may slidably receive the screw 55 or any other suitable fastener.

With continued reference to FIGS. 1-1A, the second end member 42 includes a posterior surface 58, a distal surface 60, an angled surface 62, a depression 64 and lateral surfaces 66, 68. The posterior surface 58 is shaped to conform over the second outer circumferential surface 33 of the vertebral body 32 of the superior vertebra 14. The distal surface 60, which is adjacent the posterior surface 58, is shaped to conform to the surface on the pedicle root portion 35 of the superior pedicle 34. An angled surface 62 lies opposed from the posterior face 58. The angled surface 62 is suitably shaped and dimensioned to allow insertion of an anchor such as a screw 55 (shown in phantom) generally from the intervertebral foramen region, into and through the body of the second end member 42, and the pedicle 34. The angled surface 62 further includes an aperture 65 adapted to threadably receive the screw 55. Alternatively, the aperture 65 may slidably receive the screw 55 or any other suitable fastener. A depression 64 generally located opposite from the posterior surface 58 further defines the second end member 42, contains the angled surface 62, and is suitably shaped and dimensioned to permit insertion of the screw 55.

While the surfaces respectively defining the first and second end members 40, 42 are depicted and described with details pertaining to the exemplary embodiment of FIGS. 1-1A, any other combination of surfaces is contemplated, so long as they are able to fit within the intervertebral foramen, conform generally to the outer circumferential surfaces 23, 33 defining the vertebral body, and the pedicle root portions of the pedicles 24, 34 and permit insertion of fasteners such as screws to facilitate coupling of the spreading device 10 to the surrounding vertebral surfaces.

With reference to FIG. 1A, the first and second end members 40, 42 are generally made of a rigid material such as titanium or alloys thereof or any other metal or composite material, such that the end members 40, 42 can maintain structural rigidity and be suitable for human surgical implantation.

The central portion 44 is coupled to or integrally formed with the first and second end members 40, 42, has a generally prismatic shape and is made of a resilient material such as polycarbonate urethane ("PCU") or any other elastic polymer. Fiber reinforcement of the resilient material may be desirable to prevent creep. The central portion 44 in this exemplary embodiment includes a posterior curve so as to allow for minimized obstruction, if required, of nerve roots, the psoas muscle or other structures. The central portion 44 applies a distraction force to the foramen, thereby spreading the inferior and superior vertebrae 12,14 apart, while allowing, due to the flexibility of the material that defines the central portion 44, a greater segmental range of motion compared to ranges of motion provided by known spinal fixation devices.

Figure 2:
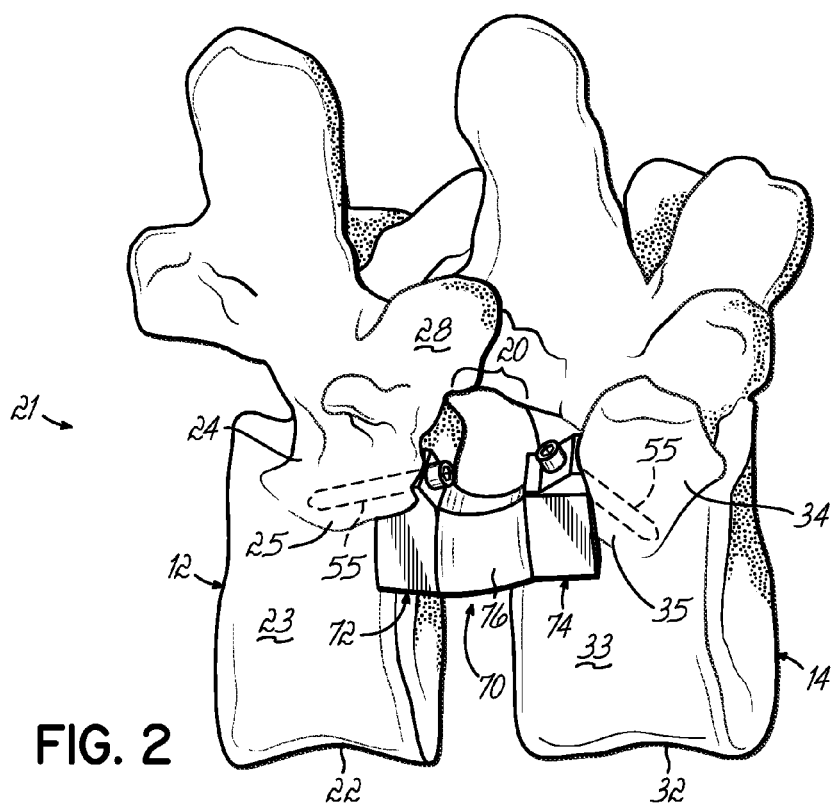
FIG. 2 is a perspective view of an alternative embodiment of a spreading device implanted in an intervertebral foramen.

With reference to FIG. 2, in which like reference numerals refer to like features in FIG. 1, an alternative embodiment of a spreading device 70 is shown deployed in the intervertebral foramen 20. The surrounding anatomical structure is the same as that described for the embodiment of FIG. 1, the description of which may be referred to for an understanding of the anatomical structure in FIG. 2 as well. The spreading device 70, like the spreading device 10 of FIGS. 1-1A, is a generally elongate body defined by two opposed first and second end members 72, 74 and a resilient central portion 76 there between. The spreading device 70 is shown deployed in a generally linear cephalo-caudal relationship between the inferior and superior vertebrae 12, 14 such that the first and second end members 72, 74 are respectively in a confronting relationship with the first and second outer circumferential surfaces 23, 33 and respective pedicle root portions 25, 35 of the inferior and superior vertebrae 12, 14. Each of the first and second end members 72, 74 is irregularly shaped and is made of metal or any other material suitable to maintain rigidity of the device 70 while being suitable for human surgical implantation.

Figure 2A:
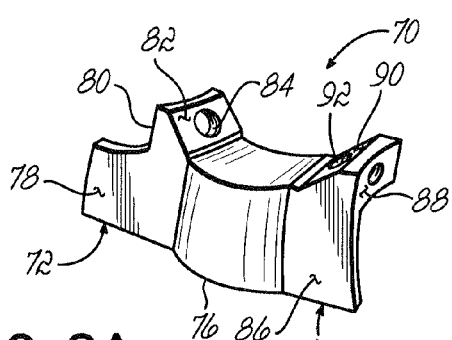
FIG. 2A is a perspective view of the spreading device of FIG. 2.

With reference to FIGS. 2-2A, the first end member 72 is defined by a lateral plate 78, a top face 80 and a front face 82. The lateral plate 78 is shaped and dimensioned to conform to the outer circumferential surface 23 of the inferior vertebral body 22. The top face 80 is shaped and dimensioned to conform to the pedicle root portion 25 of the pedicle 24 such that, in cooperation with the lateral plate 78, the first end member 72 can securely fit over a portion of the inferior vertebra 12 defining the intervertebral foramen 20, such that the first end member 72 is restricted from movement in at least two directions. The front face 82 is an angled surface adjacent the lateral plate 78 and top face 80 and includes a threaded aperture 84 suitable to receive a fastener in the form of a screw 55. Alternatively, the aperture 84 may not be threaded and may be adapted to receive any suitable fastener other than a screw 55. The front face 82 is angled such that a screw 55 or other fastener can be inserted into and through the body of the first end member 72 from the intervertebral foramen 20 and into the pedicle 24, to thereby secure the first end member 72 in place against the inferior vertebra 12.

The second end member 74 is defined by a lateral plate 86, a bottom face 88 and a front face 90. The lateral plate 86 is shaped and dimensioned to conform to the outer circumferential surface 33 of the superior vertebral body 32. The bottom face 88 is shaped and dimensioned to conform to the pedicle root portion 35 of the pedicle 34 such that, in cooperation with the lateral plate 86, the second end member 74 can securely fit over a portion of the superior vertebra 14 defining the intervertebral foramen 20, such that the first end member 72 is restricted from movement in at least two directions. The front face go is an angled surface adjacent the lateral plate 86 and bottom face 88 and includes a threaded aperture 92 suitable to receive a fastener in the form of a screw 55. Alternatively, the aperture 92 may not be threaded and may be adapted to receive any suitable fastener other than a screw 55. The front face 90 is angled such that a screw 55 or other fastener can be inserted into and through the body of the second end member 74 from the intervertebral foramen 20 and into the pedicle 34, to thereby secure the second end member 74 in place against the superior vertebra 14.

With reference to FIG. 2A, the central portion 76 is coupled to or integrally formed with the first and second end members 74, 76, has a generally prismatic shape and is made of a resilient material such as polycarbonate urethane ("PCU") or any other elastic polymer. Fiber reinforcement of the resilient material may be desirable to prevent creep. The central portion 76 in this exemplary embodiment includes an anterior curve so as to allow for minimized obstruction, if required, of nerve roots, the psoas muscle or other structures. The central portion 76 applies a distraction force to the foramen, thereby spreading the inferior and superior vertebrae 12,14 apart, while allowing, due to the flexibility of the material that defines the central portion 76, a greater segmental range of motion compared to ranges of motion provided by known spinal fixation devices.

Figure 3:
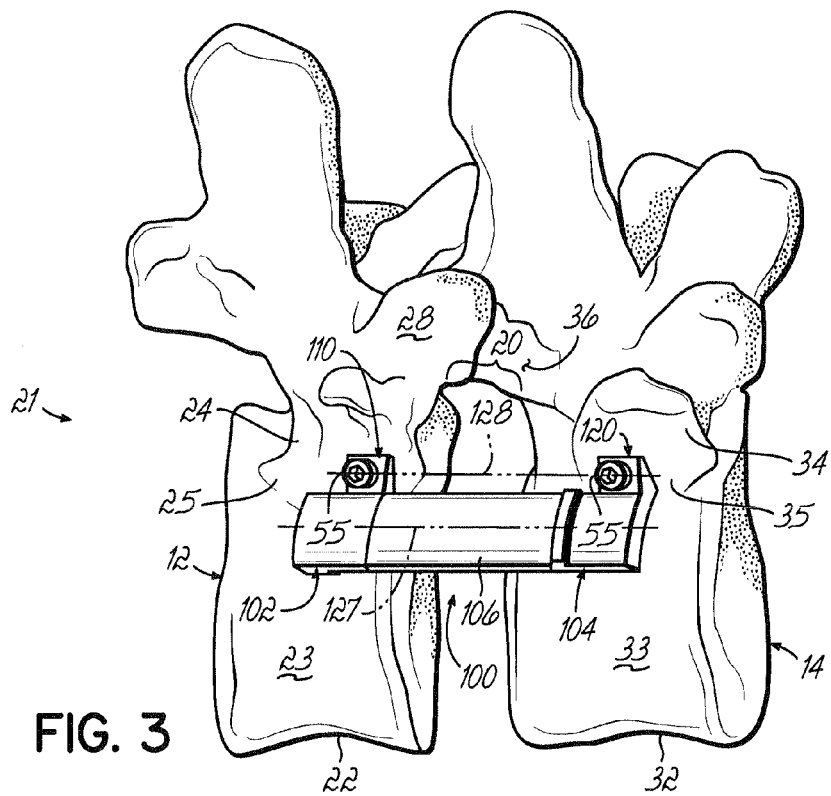
FIG. 3 is a perspective view of an alternative embodiment of a spreading device implanted in an intervertebral foramen.

With reference to FIG. 3, in which like reference numerals refer to like features in FIGS. 1, 2, an alternative embodiment of a spreading device 100 is shown deployed in the intervertebral foramen 20. The surrounding anatomical structure is the same as that described for the embodiment of FIG. 1, the description of which may be referred to for an understanding of the anatomical structure in FIG. 3 as well. The spreading device 100, like the spreading devices 10, 70 of respective FIGS. 1, 2, is a generally elongate body defined by two opposed first and second end members 102, 104 and a resilient central portion 106 there between. The spreading device 100 is shown deployed in a generally linear cephalo-caudal relationship between the inferior and superior vertebrae 12, 14 such that the first and second end members 102, 104 are respectively in a confronting relationship with the first and second outer circumferential surfaces 23, 33 and respective pedicle root portions 25, 35 of the inferior and superior vertebrae 12, 14. Each of the first and second end members 102, 104 is irregularly shaped and is made of metal or any other material suitable to maintain rigidity of the device 100 while being suitable for human surgical implantation.

Figure 3A:
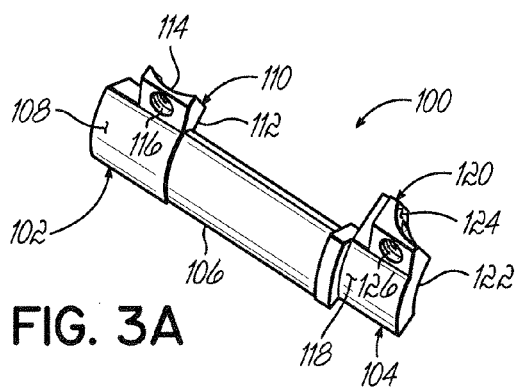
FIG. 3A is a perspective view of the spreading device of FIG. 3.

With reference to FIGS. 3-3A, the first end member 102 is defined by a main body portion 108 and a lateral flange 110 extending from the main body portion 108. The main body portion 108 is partially defined by a back surface 112 shaped and dimensioned to conform to the outer circumferential surface 23 of the inferior vertebral body 22. The lateral flange 110 is partially defined by a back surface 114 shaped and dimensioned to conform to the pedicle root portion 25 of the pedicle 24 such that, in cooperation with the main body portion 108, the first end member 102 can securely fit over a portion of the inferior vertebra 12 defining the intervertebral foramen 20, such that the first end member 102 is restricted from movement in at least two directions. The lateral flange 110 includes a threaded aperture 116 suitable to receive a fastener in the form of a screw 55. Alternatively, the aperture 116 may not be threaded and may be adapted to receive any suitable fastener other than a screw 55. A screw 55 or other fastener can be inserted into and through the body of the lateral flange 110 and into the pedicle 24, to thereby secure the first end member 102 in place against the inferior vertebra 12.

The second end member 104 is defined by a main body portion 118 and a lateral flange 120 extending from the main body portion 118. The main body portion 118 is partially defined by a back surface 122 shaped and dimensioned to conform to the outer circumferential surface 33 of the superior vertebral body 32. The lateral flange 120 is partially defined by a back surface 124 shaped and dimensioned to conform to the pedicle root portion 35 of the pedicle 34 such that, in cooperation with the main body portion 118, the second end member 104 can securely fit over a portion of the superior vertebra 14 defining the intervertebral foramen 20, such that the second end member 104 is restricted from movement in at least two directions. The lateral flange 120 includes a threaded aperture 126 suitable to receive a fastener in the form of a screw 55. Alternatively, the aperture 126 may not be threaded and may be adapted to receive any suitable fastener other than a screw 55. A screw 55 or other fastener can be inserted into and through the body of the lateral flange 120 and into the pedicle 34, to thereby secure the second end member 104 in place against the superior vertebra 14.

With continued reference to FIGS. 3-3A, the central portion 106 is coupled to or integrally formed with the first and second end members 102, 104, has a generally prismatic shape and is made of a resilient material such as polycarbonate urethane ("PCU") or any other elastic polymer. Fiber reinforcement of the resilient material may be desirable to prevent creep. The central portion 106 in this exemplary embodiment is generally straight but it may alternatively be curved or have any other shape so as to allow for minimized obstruction, if required, of nerve roots, the psoas muscle or other anatomical structures. The central portion 106 applies a distraction force to the intervertebral foramen 20, thereby spreading the inferior and superior vertebrae 12,14 apart, while allowing, due to the flexibility of the material that defines the central portion 106, a greater segmental range of motion compared to ranges of motion provided by known spinal fixation devices.

The lateral flanges 110, 120 and the respective apertures 116, 126 are laterally offset from the main body portions 108, 118 such that potential obstruction of nerve roots and other anatomical structures is minimized. Moreover, lateral offsetting of the points of coupling of the end members 102, 104 to the respective vertebrae 12, 14 permits localization of the distraction force described above along a first axis 127 lateral to a second axis 128 joining the apertures 116, 126 respectively lying on lateral flanges 110, 120.

Figure 4:
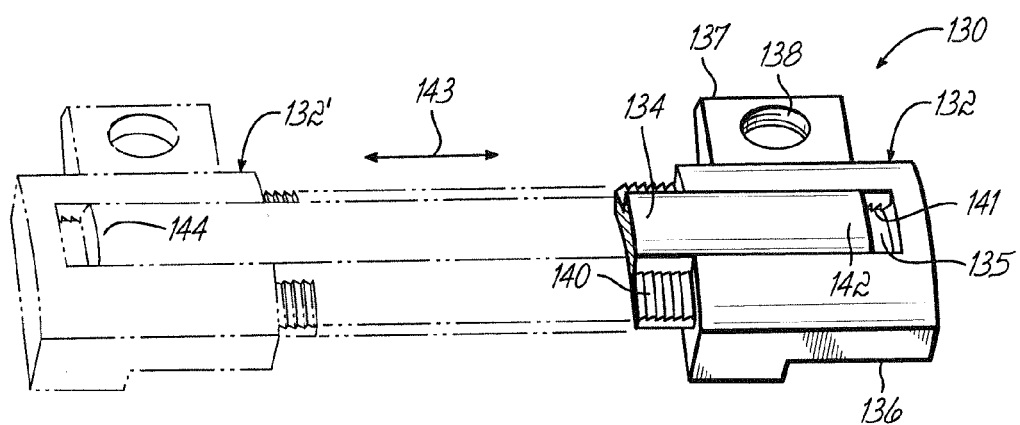
FIG. 4 is a perspective view of an alternative embodiment of a spreading device.

With reference to FIG. 4, an alternative embodiment of a spreading device 130 includes an end member 132 and an adjustable resilient member 134. The end member 132 includes a bottom face 136 shaped and dimensioned to conform to one or more of the vertebral structures defining the intervertebral foramen, including but not limited to, and in reference to FIG. 1, an outer circumferential surface 23, 33, pedicle root portions 25, 35 and pedicles 24, 34. Such conformation restricts the movement of the end member 132 in one or more directions, thereby permitting it to securely fit in an intervertebral foramen 20. The end member 132 further includes a laterally projecting flange 137 that includes an aperture 138 which may or may not be threaded. The aperture 138 is adapted to receive a fastener such as a screw (not shown) there through, such that the fastener can secure the end member 132 against the anatomical structure to which the bottom face 136 conforms.

The spreading device 130 includes a resilient member 134 having a longitudinal axis and similar in materials to the resilient members 44, 76, 106 (FIGS. 1A, 2A, 3A), the respective descriptions of which may be referred to for an understanding of the resilient member 134 as well. The resilient member 134 includes a ratchet portion 140 ratchetly engaged with the end member 132 along a cooperating ratchet surface 141. Thus, the position of the resilient member 134 may be adjusted generally in a direction as indicated by arrow 143 and within a channel 135 in the body of the end member 132. The material defining the resilient member 134, therefore must, in addition to the requirements set forth in regards to the resilient members 44, 76, 106, be such that it allows for ratchetly interlocking engagement with a ratchet surface of any suitable rigid material such as a metal.

With continued reference to FIG. 4, the resilient member 134 is coupled to the end member 132 such that it is restricted from uncoupling therefrom. Consequently, any additional suitable components or constructs capable of providing such coupling are contemplated including but not limited to tongue and groove components and the like (not shown) respectively along sides defining the channel 135 and portions of the resilient member 134 confronting such sides. In one aspect of this embodiment, the ratchetly engagement may be such that movement of the resilient member 134 with respect to the end member 132 may made in only one direction, such as away from the end member 132, with a restriction against movement of the resilient member 134 in the opposite direction.

The resilient member 134 includes opposed proximal and distal ends 142, 144 such that the proximal end 142 is coupled as described above to the end member 132 while the distal end 144 is adapted to be coupled in a similar fashion to another end member 132' (shown in phantom). Persons of ordinary skill in the art will appreciate that the distal end 144 may be adapted to be coupled to an end member 132' similar to the end member 132 or alternatively to an end member similar to any of the end members described above with reference to the spreading devices 10, 70, 100 or any variation thereof.

With continued reference to FIG. 4, the adjustable axial position of the resilient member 134 with respect to the end member 132 optimizes fixation of the spreading device 130 to any of the anatomical structures defining an intervertebral foramen 20 (FIG. 1), by allowing adjustability of the position of the opposing end member such as the exemplary end member 132', until a desired level of conformation to surfaces of such anatomical structures is achieved. The adjustable axial position of the resilient member 134, which in turn controls its exposed length, further permits control of the flexibility and rigidity of the spreading device 130, which is partly determined by such exposed length. While one embodiment of a mechanism which provides adjustability of the resilient member 134 is shown and described herein, other adjustability mechanisms can readily be utilized within the scope of this invention and the appended claims.

Figure 5:
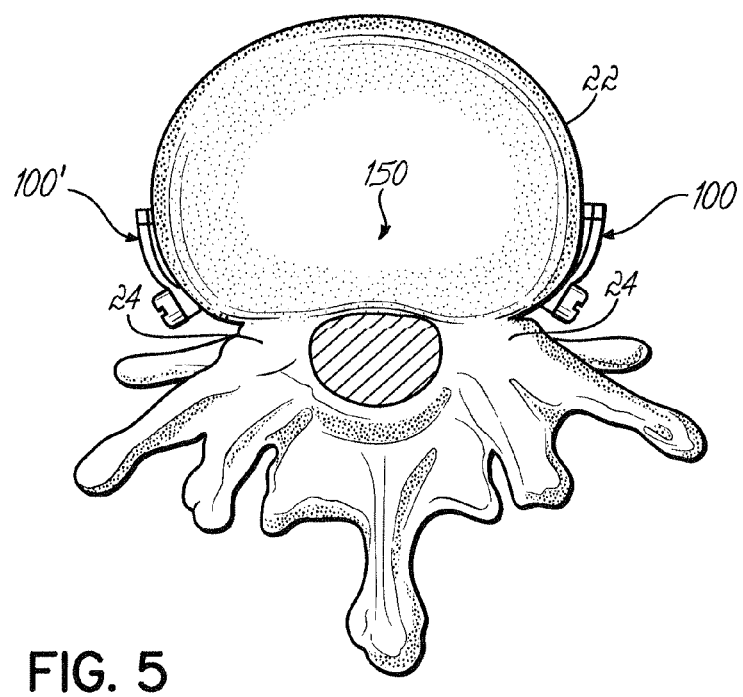
FIG. 5 is a top view of a spine segment having two implanted spreading devices.

With reference to FIG. 5, in which like reference numerals refer to like features in FIGS. 3-3A, an exemplary implantation of the spreading device 100 is shown. While the spreading device 100 is used for purposes of illustration, persons of ordinary skill in the art will appreciate that this exemplary implantation is similarly applicable to the spreading devices 10, 70, 130 (respectively FIGS. 1A, 2A, 4) or any variations thereof. Two of such spreading devices 100, 100' are shown implanted on generally diametrically opposed sides of the vertebral bodies 22, 32. Alternatively one such spreading device or any number in excess of two may be implanted.

With reference to FIGS. 1-5, while all exemplary embodiments are depicted having a unitary resilient member and end members each including only one aperture, persons of ordinary skill in the art will appreciate that, alternatively, spreading devices in accordance with the principles of the present invention may include non-unitary resilient members, such as resilient members made up of more than one elongate block, as well as include more than one aperture in any of the end members.

Advantageously, the spreading devices 100, 100' may be positioned at positions generally proximate the natural center of rotation 150 of a vertebral body 22, 32, such that the distraction force exerted thereby does not substantially move or alter the location of the center of rotation 150 of the vertebrae 12, 14.

Accordingly, many further embodiments, applications and modifications of the invention will become readily apparent to those of ordinary skill in the art without departing from the scope of the invention and applicant intends to be bound only by the claims appended hereto.

What is claimed is:

1. A spinal device for spreading of first and second vertebral elements, each of the first and second vertebral elements having a circumferential surface defining a vertebral body and a pedicle having a pedicle root portion adjacent the circumferential surface, comprising:
    a first end member having at least one surface adapted to conform to at least one of the circumferential surface and the pedicle root portion of the first vertebral element;
    a second end member having at least one surface adapted to conform to at least one of the circumferential surface and the pedicle root portion of the second vertebral element; and
    a resilient member extending between said first and second end members and being adapted to exert a force against the first and second vertebral elements;
    wherein the resilient member is formed of a flexible elastic material maintaining segmental motion between the first and second vertebral elements when secured therebetween.

2. The spinal device of claim 1 further comprising at least one aperture in each of said first and second end members, said aperture being adapted to direct a bone anchor into at least one of the pedicle root portion and the vertebral body.

3. The spinal device of claim 2 wherein:
    said first end member further comprises a main body portion; and
    said at least one aperture is laterally offset from said main body portion.

4. The spinal device of claim 2 wherein:
    said first end member further comprises an exposed surface angled to be in a confronting relationship with an intervertebral foramen; and
    said at least one aperture extends from said exposed surface.

5. The spine device of claim 4 wherein:
    said second end member further comprises an exposed surface angled to be in a confronting relationship with an intervertebral foramen; and
    said at least one aperture extends from said exposed surface.

6. The spinal device of claim 1 wherein said resilient member comprises polycarbonate urethane.

7. A spinal device for spreading of first and second vertebral elements, each of the first and second vertebral elements having a circumferential surface defining a vertebral body and a pedicle having a pedicle root portion adjacent the circumferential surface, comprising:
    a first end member having at least one surface adapted to conform to at least one of the circumferential surface and the pedicle root portion of the first vertebral element;
    a second end member having at least one surface adapted to conform to at least one of the circumferential surface and the pedicle root portion of the second vertebral element; and
    a resilient member extending from and ratchetly engaged with said first end member;
    wherein said resilient member is coupled to said second end member and is further adapted to exert a force against the first and second vertebral elements;
    wherein the resilient member is formed of a flexible elastic material maintaining segmental motion between the first and second vertebral elements when secured therebetween.

8. The spinal device of claim 7 wherein said resilient member is ratchetly coupled to said second end member.

9. The spinal device of claim 7 wherein said resilient member comprises polycarbonate urethane.

10. The spinal device of claim 7 wherein said first end member further comprises at least one aperture adapted to direct a bone anchor into at least one of the pedicle root portion and the vertebral body.

11. The spinal device of claim 10 wherein:
    said first end member further comprises a main body portion; and
    said at least one aperture is laterally offset from said main body portion.

* * * * *